United States Patent [19]

Dunn

[11] Patent Number: 4,520,009

[45] Date of Patent: May 28, 1985

[54] SUSTAINED RELEASED ASPIRIN FORMULATION

[75] Inventor: James M. Dunn, Englewood, Colo.

[73] Assignee: Verex Laboratories, Inc., Englewood, Colo.

[21] Appl. No.: 555,700

[22] Filed: Nov. 28, 1983

[51] Int. Cl.³ .................... A61K 31/60; A61K 31/74
[52] U.S. Cl. ........................................ 424/78; 514/161
[58] Field of Search .................................. 424/78, 230

[56] References Cited

U.S. PATENT DOCUMENTS 4,375,468  1/1983  Dunn .................................. 424/230

*Primary Examiner*—Stanley J. Friedman
*Attorney, Agent, or Firm*—Niblack & Niblack

[57] ABSTRACT

A constant release aspirin tablet comprising from 85–95 weight percent of aspirin, from 1.5–5 weight percent of microcrystalline cellulose, from 1–10 weight percent of cellulose acetate phthalate, from 0.75–4 weight percent of a plasticizer, from 0.75–5 weight percent of corn starch, and from 0.5 to 2 percent of a lubricant.

12 Claims, No Drawings

SUSTAINED RELEASED ASPIRIN FORMULATION

BACKGROUND OF THE INVENTION

The present invention relates to improved aspirin formulations, and more specifically relates to an improved constant release aspirin formulation which is readily reproducible on a commercial basis.

Attempts to develop a timed release aspirin product which will provide a more constant level of aspirin in the blood over a prolonged period of time have been in progress since at least 1953. (See Press, U.S. Pat. No. 2,953,497.) and a substantial body of prior art exists which is directed specifically to timed or sustained release aspirin formulations, also referred to as prolonged release, constant release, controled release and the like. See, for example, U.S. Pat. Nos. 3,488,418, 3,341,416, 3,155,590, 3,247,066, 3,115,411, 3,632,739, 4,012,498, 3,362,881, 4,308,251 and commonly assigned U.S. Pat. No. 4,375,468.

Commonly assigned Guy et al U.S. Pat. Nos. 4,025,613 and 3,906,086 disclose one such product, a timed-release aspirin tablet which is made by coating particles of aspirin prior to tabletting with cellulose acetate phthalate and a plasticizer. While aspirin tablets prepared by the process of the Guy et al patents exhibit the desired in vitro constant release properties, and satifactory tablets are produced in experimental quantities, difficulties are encountered in larger, commercial production runs.

The present invention provides an improved cellulose acetate phthalate-plasticizer matrix formulation which not only exhibits the desired constant release rate properties, but eliminates the problems encountered with the Guy et al process and formulations when aspirin tablets are produced in large batches, as is necessary for commercial production.

SUMMARY OF THE DISCLOSURE

The constant release aspirin tablets of the present invention comprise from 85-95 weight percent of aspirin, from 1.5-5 weight percent of microcrystalline cellulose, from 1-10 weight percent of cellulose acetate phthalate, from 0.75-4 weight percent of a plasticizer, from 0.75-5 weight percent of corn starch, and from 0.1 to 2 percent of a lubricant.

DETAILED DESCRIPTION OF PREFERRED EMBODIMENTS

The constant order release aspirin tablet of the present invention comprises an intimate, compressed admixture of from 85-95 weight percent, preferably 88-93 weight percent and most preferably 89.00 weight percent of aspirin, from 1.5-5, preferably 2-3.4 and most preferably 2.67 weight percent of microcrystalline cellulose (Avicel), from 1-10, preferably 2-4 and most preferably 2.67 weight percent of cellulose acetate phthalate, from 0.75-5 weight percent, preferably 1.5 to 2.5 and most preferably 1.78 weight percent of a plasticizer, from 0.75-5, preferably 2-4 and most preferably 2.88 of corn starch, and from 0.5 to 2.0, preferably from 0.75 to 1.4, most preferably, 1.0 weight percent of a lubricant.

The preferred plasticizer is polyethylene glycol 8000, although a number of pharmaceutically acceptable plasticizers may be employed. Representative plasticizers include, but are not limited to those disclosed in Hotko et al. U.S. Pat. No. 3,325,365 and Gaunt U.S. Pat. No. 3,449,489, i.e., esters of carboxylic acid such as lower alkyl citrates, e.g. triethyl citrate and the like, acetyltributyl citrate, acetyltriethyl citrate, other phthalate esters such as dimethyl phthalate, and other esters such as benzyl benzoate.

Suitable lubricants include talc, magnesium stearate, stearic acid, and the like, alone or in combination.

The term "constant order release aspirin tablet", as used herein, refers to an aspirin tablet wherein the in vitro release of aspirin from the tablet, using a USP dissolution apparatus, pH 7.5 is constant and linear against time until all the aspirin is released. When plotted on an x,y graph, using the formula $k=dc/dt$ wherein $k$=constant, $dc$=decreasing concentration, and $dt$=decreasing time, a straight line is formed. Calculation of the data points by linear regression gives an r value of 0.85–1.0. An r value of 1.0 is a perfect straight line.

In addition to the properties of the formulation of the present invention, the prior art problems encountered with attempting to produce large quantities of sustained release aspirin tablets is further overcome by the process of the present invention.

The following Examples further illustrate the present invention.

EXAMPLE 1

Aspirin tablets containing 650 mg of aspirin and weighing an average of 735 mg were prepared from 10 kilograms of the following formulation:

| Ingredient | Weight Percent |
| --- | --- |
| Aspirin | 89.00 |
| Microcrystallne Cellulose(Avicel) | 2.67 |
| Cellulose Acetate Phthalate | 2.67 |
| Polyethylene Glycol 8000(Carbowax 8000) | 1.78 |
| Corn Starch | 2.88 |
| Talc | 1.00 |
| Acetone | 2000 ml |
| Methylene Chloride | 1000 ml |

The aspirin, Avicel and corn starch were blended and placed in a Hobart mixer. Cellulose acetate phthalate, dissolved in acetone, and Carbowax 8000, dissolved in methylene chloride are blended until a uniform, viscous mixture is obtained. The cellulose acetate phthalate-Carbowax mixture was slowly added to the aspirin blend with constant stirring until a uniform wet granular mass was obtained. The material was discharged onto trays and dried at 125° F. for 1-2 hours. The dried granulate was then screened through a number A screen, blended with talc and compressed on a rotary press.

EXAMPLE 2

To determine if the formulation of Example 1 produced constant release rate tablets, 6 tablets weight an average of 735 mg were placed in an approved U.S.P. dissolution analysis and assayed for aspirin content. The average amount of aspirin per tablet was reported as 649.7. Dissolution was carried out using U.S.P. apparatus II, pH 7.5, 150 rpm at 37° C. Linear regression analysis of the mean percent of drug released shows a r value of 0.994.

The above examples have been set forth for illustrative purposes only. It will be apparent to those skilled in the art that variations and modifications may be made without departing from the spirit and scope of the invention.

The invention claimed is:

1. A constant release aspirin tablet comprising from 85–95 weight percent of aspirin, from 1.5–5 weight percent of microcrystalline cellulose, from 1–10 weight percent of cellulose acetate phthalate, from 0.75–4 weight percent of a plasticizer, from 0.75–5 weight percent of a pharmaceutically acceptable diluent, and from 0.5 to 2 percent of a lubricant.

2. The aspirin tablet of claim 1 wherein said plasticizer is a high molecular weight polyethylene glycol.

3. The aspirin tablet of claim 1 wherein said plasticizer is polyethylene glycol 8000.

4. The aspirin tablet of claim 1 wherein the diluent is corn starch.

5. The aspirin tablet of claim 2 wherein the diluent is corn starch.

6. The aspirin tablet of claim 3 wherein the diluent is corn starch.

7. The aspirin tablet of claim 1 wherein said lubricant is talc.

8. The aspirin tablet of claim 3 wherein said lubricant is talc.

9. The aspirin tablet of claim 4 wherein said lubricant is talc.

10. The aspirin tablet of claim 5 wherein said lubricant is talc.

11. The aspirin tablet of claim 6 wherein said lubricant is talc.

12. A constant order release aspirin tablet comprising from 85–95 weight percent of aspirin, from 1.5–5 weight percent of microcrystalline cellulose, from 1–10 weight percent of cellulose acetate phthalate, from 0.75–4 weight percent of polyethylene glycol 8000, from 0.75 to 5 weight percent of corn starch and from 0.5 to 2 weight percent of talc.

* * * * *